United States Patent [19]

Komiya

[11] 4,325,374
[45] Apr. 20, 1982

[54] HIGH FREQUENCY ELECTROSURGICAL INSTRUMENT FOR AN ENDOSCOPE

[75] Inventor: Osamu Komiya, Hachioji, Japan

[73] Assignee: Olympus Optical Co., Ltd., Tokyo, Japan

[21] Appl. No.: 154,441

[22] Filed: May 29, 1980

[30] Foreign Application Priority Data

Jun. 4, 1979 [JP] Japan .............................. 54-75744[U]

[51] Int. Cl.³ ............................................. A61B 17/39
[52] U.S. Cl. ............................................. 128/303.15
[58] Field of Search ...................... 128/303.13, 303.14, 128/303.15, 303.16, 303.17, 320

[56] References Cited

U.S. PATENT DOCUMENTS

| | | | |
|---|---|---|---|
| 1,741,740 | 12/1929 | Sederholm et al. | 128/303.15 |
| 3,903,892 | 9/1975 | Komiya | 128/303.15 |
| 3,910,279 | 10/1975 | Okada et al. | 128/303.15 |
| 4,181,131 | 1/1980 | Ogiu | 128/303.15 |

FOREIGN PATENT DOCUMENTS

| | | | |
|---|---|---|---|
| 2426781 | 12/1975 | Fed. Rep. of Germany | 128/303.15 |
| 2657256 | 6/1978 | Fed. Rep. of Germany | 128/303.15 |
| 5319038 | 5/1978 | Japan | 128/303.15 |

*Primary Examiner*—Lee S. Cohen
*Attorney, Agent, or Firm*—Frishauf, Holtz, Goodman and Woodward

[57] ABSTRACT

A high frequency electrosurgical instrument for an endoscope comprises a flexible tube which has at a distal end portion a pair of wire guiding holes spaced from each other in the axial direction of the tube. In the distal end portion of the tube a flexible coil is inserted, which extends at least between the wire guiding holes. An electrode wire extends in the tube from a distal end of the flexible coil, comes out of the tube through the wire guiding hole located adjacent to the distal end of the tube, reenters the tube through the wire guiding hole located adjacent to the proximal end of the tube and through a pair of turns of the coil which are located near the latter wire guiding hole, extends through the tube to the proximal end of the tube, and is connected to a high frequency power source. The electrode wire is reciprocable within the tube, except for its distal end portion. The flexible coil prevents said electrode wire from cutting the tube to form a slit extending from either wire guiding hole and prevents said tube from collapsing.

17 Claims, 12 Drawing Figures

HIGH FREQUENCY ELECTROSURGICAL INSTRUMENT FOR AN ENDOSCOPE

BACKGROUND OF THE INVENTION

This invention relates to a high frequency electrosurgical instrument used in an endoscope, which is provided at its distal end portion with an electrode wire supplied with a high frequency current and which is inserted into a coeliac cavity through an endoscope in order to cut an affected part.

A known electrosurgical instrument of this type is constructed as shown in FIG. 1. The instrument comprises a flexible tube 1 made of a synthetic resin such as fluorine resin. The tube 1 has at its distal end portion a pair of electrode wire holes 2 which are set apart in the axial direction of the tube 1. An electrode wire 3 extends through the tube 1, comes out of the tube 1 through one of the holes 2 which is remote from the distal end of the tube 1, enters the tube 1 through the other hole 2, and turns back to extend through the tube 1 to the proximal end of the tube 1 to have its end secured to the proximal end portion of the tube 1.

The tube 1 is guided through an endoscope inserted in a coeliac cavity until its distal end portion is placed near the coeliac cavity. Then, an operation section provided at the proximal end of the tube 1 is operated so as to pull the electrode wire 3. As the wire 3 is pulled, the distal end portion of the tube 1 is bent to form a bow with the wire 3 extended as a string, as illustrated in FIG. 2. That portion of the wire 3 which makes the string of the bow is brought into contact with an affected part in the coeliac cavity. A high frequency current is applied between the electrode wire 3 and the patient so that the affected part is cut.

The known electrosurgical instrument is disadvantageous in some respects. First, the wire 3 is likely to cut the tube 1 by the tension of the wire 3 and the heat produced during the high frequency electric current, thus forming a slit extending from the hole 2 in the axial direction of the tube 1. If this happens, that portion of the wire 3 which makes the string of the bow is moved downward, as shown in FIG. 3, from the position indicated by chain lines to the position indicated by solid lines. Secondly, if the wire 3 is pulled too much, the distal end portion of the tube 1 is collapsed at the middle point as shown in FIG. 4.

SUMMARY OF THE INVENTION

An object of this invention is to provide a high frequency electrosurgical instrument for an endoscope, which can be readily operated without having its flexible tube cut axially by an electrode wire or collapsed at the distal end portion.

A high frequency electrosurgical instrument according to this invention has a flexible tube which is made of a synthetic resin. The distal end portion of the flexible tube has a pair of electrode wire guiding holes which are set apart in the axial direction of the tube. A reinforcing coil of a resilient metal is provided within the flexible tube and lies at least between said holes. An electrode wire is secured at one end to an operation section which is provided at the proximal end of the flexible tube. The wire extends through the tube from the proximal end of the tube, comes out of the tube through a gap between two adjacent turns of the coil and through the hole located near said turns of coil and closer to the proximal end of the tube than the other hole, reenters the tube through the other hole. The other end of the wire is set stationary in the tube.

The electrode wire is pulled, when the operation section is pulled. When pulled, the wire bends the distal end portion of the flexible tube in the form of a bow and is stretched straight between the holes of the tube. However hard it is pulled, the wire will not cut the tube to form a slit extending from either hole in the axial direction of the tube. This is because it is held between two adjacent turns of the reinforcing coil. Even if it is bent to form an arc of a small radius, the distal end portion of the tube, reinforced by the reinforcing coil, will not collapse at the middle point.

BRIEF DESCRIPTION OF THE DRAWINGS

This invention can be fully understood from the following detailed description with reference to the accompanying drawings, in which.

DETAILED DESCRIPTION OF THE PREFERRED EMBODIMENTS

Figure 1:
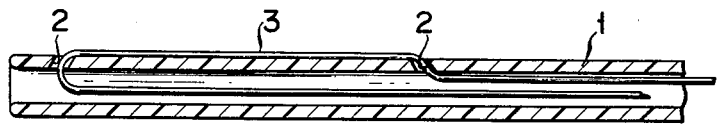
FIG. 1 is a longitudinal cross sectional view of the main part of a high frequency electrosurgical instrument of known type.
Figure 2:
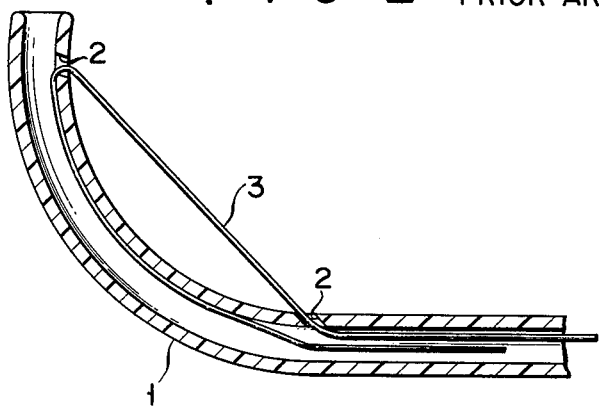
FIG. 2 is a longitudinal cross sectional view of the main part of the known instrument, with an electrode wire pulled so that the instrument can be used.
Figure 3:
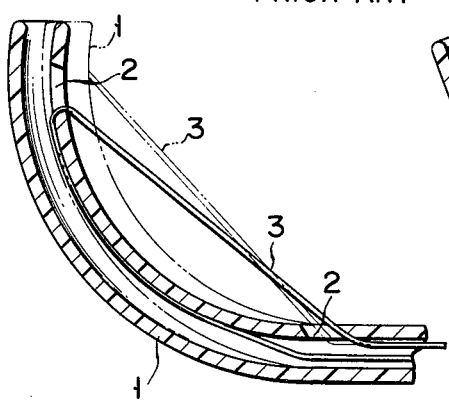
FIG. 3 is a longitudinal cross sectional view of the main part of the known instrument, with the electrode wire cutting a tube, thus forming slits extending respectively from the electrode wire guiding holes of the tube.
Figure 4:
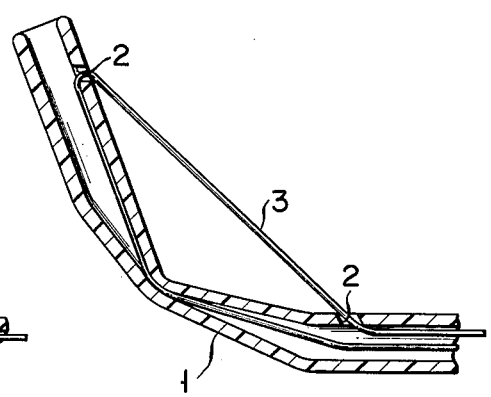
FIG. 4 is a longitudinal cross sectional view of the main part of the known instrument, with the tube collapsed at the distal end portion.

Now referring to FIGS. 5 to 8, a high frequency electrosurgical instrument according to this invention will be described. The instrument has a hollow cylindrical tube 31 made of a synthetic resin such as fluorine resin with an outer diameter of 1.5 to 2.5 mm. It is flexible and electrically insulative. The tube 31 has its diameter reduced at the open distal end. Its distal end portion 31a has a pair of holes 32a and 32b for guiding an electrode wire 33. The holes 32a and 32b are set apart in the axial direction of the tube 31.

A flexible reinforcing coil 34 is inserted in the distal end portion 31a of the tube 31. It is disposed coaxially with the tube 31, with its distal end located at the hole 32a and its proximal end located closer to the proximal end of the tube 31 than the hole 32b. The coil 34 is made of an elastic metal wire element (such as a stainless steel wire element) 0.1 to 0.3 mm thick. The pitch of the coil is about three times the diameter of the metal wire. The gap between two adjacent turns of the coil 34 is therefore substantially twice the thickness of the wire element.

The distal end 34a of the reinforcing coil 34 is located, as mentioned above, adjacent the hole 32a (hereinafter called "first hole"). The wire 33 is integral with the coil 34 and is thus made of said metal wire element. The wire 33 has one end connected to the distal end 34a of the coil 34. The end of the wire 33 connected to the coil 34 will hereinafter called the "distal end 33a". The wire 33 comes out of the tube 31 through the first hole 32a, extends outside the tube 31, and enters the tube 31 through the other hole 32b (hereinafter called "second hole"). It further extends through a gap between two adjacent turns 34b of the coil 34 which are located near the second hole 32b. The wire 33 extends through the tube 31 to the proximal end portion 31b of the tube 31.

A tubular connecting member 35 is partly and fixedly inserted in the proximal end portion 31b of the tube 31. The outer periphery of that portion of the connecting member 35 which is outside the tube 31 is put in screw engagement with a hollow cylindrical insulative cover 36. The insulative cover 36 is made of an electrically insulative material such as an electrically insulative synthetic resin. It covers not only the outer periphery of the connecting member 35 but also the outer periphery of the proximal end portion 31b of the tube 31. Through the insulative cover 36 and the connecting member 35 there is provided a metal rod 37 which can be moved in the axial direction of the tube 31. The rod 37 has a central through bore 38 in which the proximal end portion 33b of the electrode wire 33 is held immovably. The wire 33 is thus secured to the metal rod 37. The rod 37 is inserted in an insulative tube 39 made of an electrically insulative material such as synthetic resin and is protected by the insulative tube 39. Further, an O ring 40 is disposed between the insulative cover 36 and the metal rod 37, thereby rendering the tube 31 liquid-tight. A connection 41 is attached to the insulative cover 36. The connection 41 communicates with the interior of the tube 31 through passages both in the insulative cover 36 and the connecting member 35. The proximal end of the metal rod 37 is connected to a terminal 42 which is connected to a high frequency electrical power source 44. The outer periphery of the terminal 42 makes screw engagement with a hollow cylindrical cover 43 made of an electrically insulative material such as a synthetic resin. The cover 43 surrounds the terminal 42.

Figure 6:
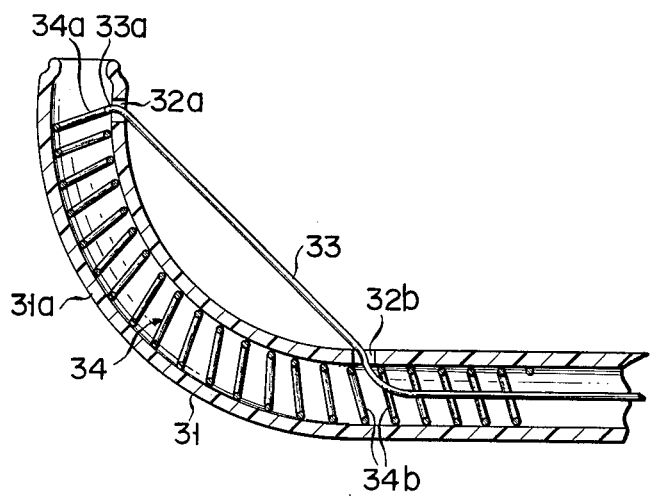
FIGS. 6 and 7 are longitudinal cross sectional views of the instrument of FIG. 5, illustrating how the main part of the instrument is used.
Figure 8:
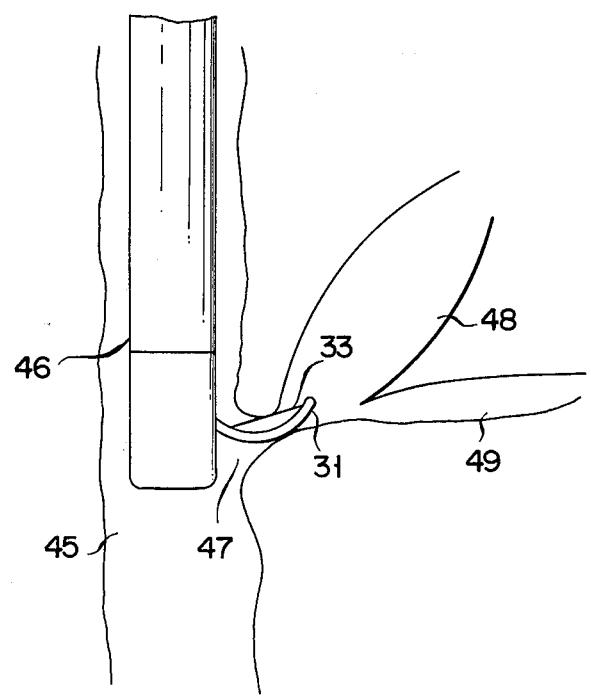
FIG. 8 shows how to use the instrument in the coeliac cavity.

Now it will be described how to operate the above-described first embodiment of the invention. First, the cover 36 is held by, for example, a left hand, and the terminal 42 is connected to the high frequency power source 44. The tube 31 is then inserted into the forceps channel of an endoscope 46 which is, as shown in FIG. 8, inserted in the duodenum 45 in preparation for cutting the duodenal papilla 47. The tube 31 is fed until its distal end portion 31a protrudes from the forceps outlet of the endoscope 46. This done, the metal 37 is pulled by operating the cover 43. As the rod 37 is pulled, the electrode wire 33 is drawn, thereby bending the distal end portion 31a of the tube 31 as illustrated in FIG. 6. The distal end portion 31a is bent in the form of a bow, with the wire 33 stretched like a bow string outside the tube 31. The electrode wire 33 is brought into contact with the duodenal papilla 47 as shown in FIG. 8. Then, as in the conventional method, an electrode (not shown) is placed on the patient's skin at the nearest position to the duodenal papilla 47. A high frequency electrical current is supplied to the electrode wire 33 so that the high frequency electrical current flows to the electrode (not shown). Such that the electrode wire 33 heat-cuts the duodenal papilla 47. Located near the duodenal papilla 47 are the cystic duct 48 and the pancreatic duct 49 as shown in FIG. 8.

As mentioned above, the wire 33 passes through a gap between the two adjacent turns 34b of the reinforcing coil which are adjacent to the second hole 32b, and its distal end 33a is connected to the distal end 34a of the reinforcing coil 34 adjacent to the first hole 32a. Thus, the tension of the wire 33 is chiefly exerted on the turns 34b of the coil 34 and the distal end of the coil 34. Thus, the holes 33a, 33b are not cut by the heat and the tension of the wire 33 so as to form axially elongated slits.

Moreover, the reinforcing coil 34, which is disposed within the distal end portion 31a of the tube 31, prevents the distal end portion 31a from collapsing, even if the electrode wire 33 is drawn strongly. This makes the electrosurgical instrument easy to operate and enhances the durability of the instrument.

Figure 7:
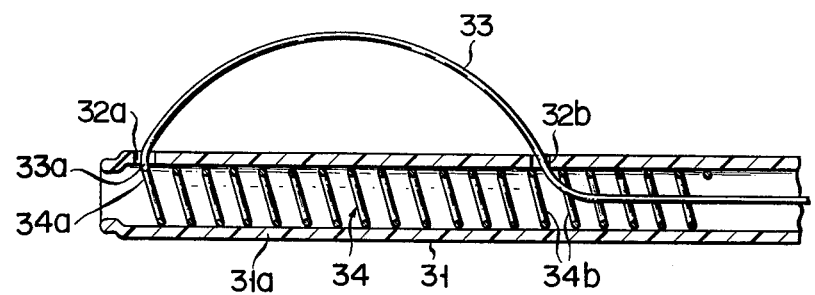

In order to cut an affected part, the electrode wire 33 may be fed so as to be curved outside the tube 31 as shown in FIG. 7, instead of being pulled to bend the distal end portion 31a of the tube 31. Also in this case, the curved portion of the wire 33 is brought into contact with the affected part.

Though the connector 41, a liquid such as a contrast medium agent may be introduced into the tube 31 and may be sprayed into a coeliac cavity from the distal end of the tube 31.

If the gap between any two adjacent turns 34b of the reinforcing coil 34 is too small, the electrode wire 33 cannot be pulled or fed smoothly. If it is too large, the coil 34 cannot smoothly guide the electrode wire 33 and cannot sufficiently reinforce the tube 31. It is therefore desired that the gap between any two adjacent turns should be about two times the diameter of the wire 33 or a little smaller.

Figure 9:
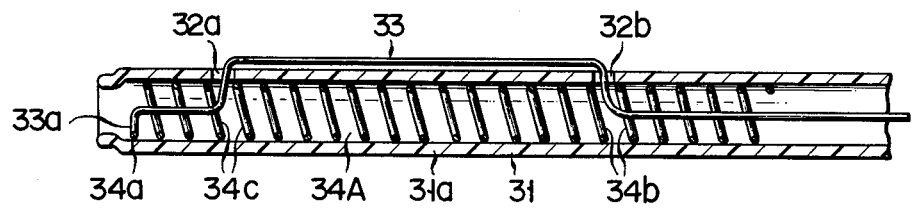
FIGS. 9 to 12 are longitudinal cross sectional views of the main part of other embodiments of high frequency electrosurgical instruments according to this invention.

FIG. 9 shows the second embodiment of the invention. In this embodiment a reinforcing coil 34A extends toward the distal end of a tube 31 beyond a first hole 32a of the tube 31. The distal end portion of an electrode wire 33 comes out of the tube 31A through a gap between two adjacent turns 34C of the coil 34A which are adjacent to the first hole 32a and then through the first hole 32a. When the wire 33 is pulled, the wire 33 chiefly contacts these turns 34C. The tension of the wire 33 thus pulled is exerted mainly on the turns 34C. The wire 33 therefore does not cut the tube 31A to form a slit extending from the first hole 32a in the axial direction of the tube 31A.

Figure 10:
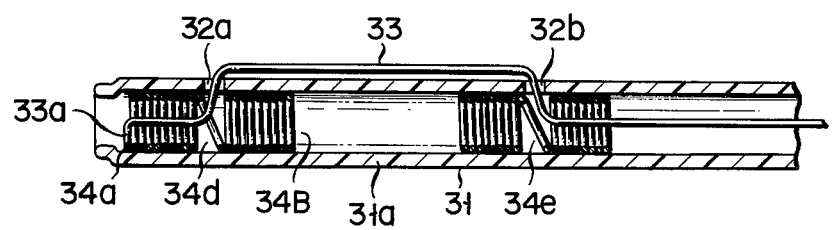

FIG. 10 shows the third embodiment of this invention. This electrosurgical instrument has a reinforcing coil 34B which portions where turns are is wound densely except that the portions 34d and 34e are sparsely wound. The reinforcing coil 34B is so positioned as to have the sparse portions 34d and 34e located adjacent to electrode wire guiding holes 32a and 32b, respectively. An electrode wire 33 of a tube 31 extends through the sparse portion 34d and the first hole 32a and then reenters the tube 31 through the second hole 32b and the sparse portion 34e. Since its turns are densely arranged over a greater part of its length, the reinforcing coil 34B is stronger than those used in the first and second embodiments and can more effectively prevent the tube 31 from collapsing.

Figure 11:
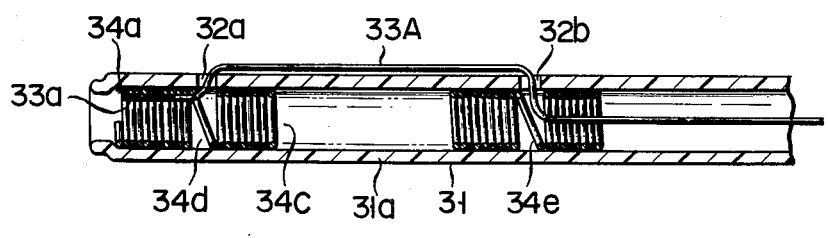

FIG. 11 shows the fourth embodiment of this invention. This electrosurgical instrument is provided with a reinforcing coil 34C which is identical in structure with the coil 34B of the third embodiment. The instrument has an electrode wire 33A which is not integral with the coil 34C and which can thus have a diameter different from that of the metal wire constituting the coil 34C. The distal end 34a of the electrode wire 33A is fixedly connected to the inner periphery of the distal end portion 34a of a reinforcing coil 34C. The fourth embodiment is advantageous in that the reinforcing coil 34C can be made of a suitable material and can have a suitable size so as to effectively prevent a tube 31 from collapsing, regardless of the material or diameter of the electrode wire 33A.

Figure 12:
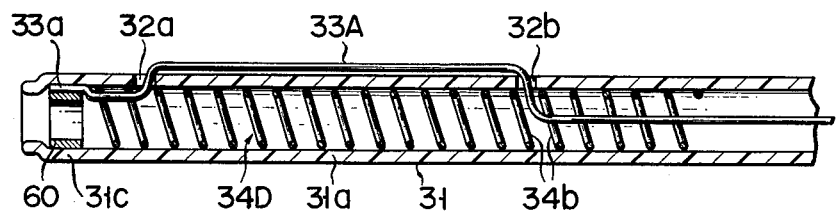

FIG. 12 shows the fifth embodiment of this invention. In this embodiment an electrode wire 33A and a reinforcing coil 34D are separate members. The distal end 33a of the wire 33A is secured to the outer periphery of a ring 60 which is securely provided in the distal end portion 31c of a flexible tube 31. Further the distal end 33a is clamped between the ring 60 and the inner periphery of the tube 31. The wire 33A and the coil 34D are provided independently in order to obtain the same merit as in the fourth embodiment.

Figure 5:
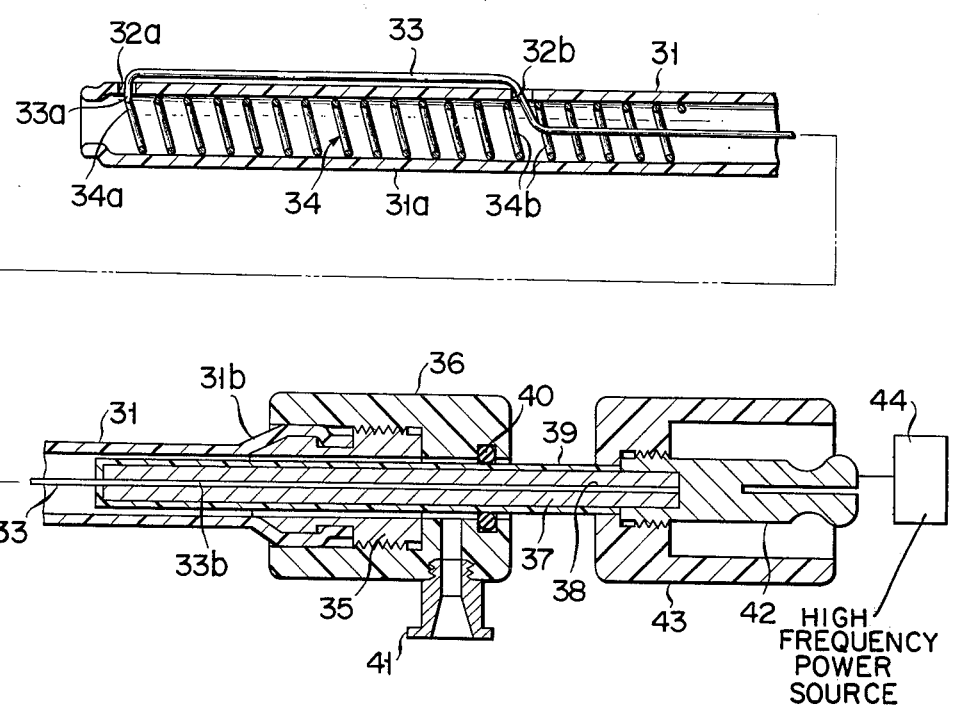
FIG. 5 is a longitudinal cross sectional view of a high frequency electrosurgical instrument according to this invention.

Except for the points mentioned above, the second to fifth embodiments shown in FIGS. 9 to 12 are identical in construction with the first embodiment shown in FIGS. 5, 6 and 7. Like and similar members of the second to fifth embodiments are identified with the same numerals as used to denote the corresponding members of the first embodiment. And the description of these members is omitted.

According to this invention, that portion of an electrode wire which is located outside a tube may be chemically etched to have a smaller diameter than the remaining portion, regardless whether the wire is integral with a reinforcing coil.

The metal wire which constitutes the electrode wire and the reinforcing coil need not to have a circular section. A metal wire having another sectional profile such as a rectangular section may be used instead.

In the embodiments of FIGS. 10 and 11, the gaps between the adjacent turns of the sparse portions 34d, 34e of the reinforcing coils 34B, 34C are substantially twice the diameter of the wire elements comprising the coils.

What is claimed is:

1. A high frequency electrosurgical instrument used in an endoscope, comprising:
    a flexible tube having a distal end, a proximal end and a distal end portion adjacent to the distal end;
    a first electrode wire guiding hole and a second electrode wire guiding hole formed in the distal end portion of said flexible tube and spaced apart axially of said flexible tube, said first electrode wire guiding hole being located closer to the distal end of said flexible tube than said second electrode wire guiding hole;
    a flexible coil having two ends, said flexible coil being inserted in the distal end portion of said flexible tube so as to prevent said distal end portion from being deformed and extending at least between said first and second electrode wire guiding holes with one end of said flexible coil being located near said first electrode wire guiding hole, said flexible coil having at least one pair of adjacent turns which are located adjacent to said second electrode wire guiding hole; and
    an electrode wire having first and second ends and an intermediate portion extending between said first and second ends, said electrode wire being reciprocable along said flexible tube, the first end of said electrode wire being disposed in said flexible tube immovably with respect to said flexible coil, said intermediate portion of said electrode wire extending out of said flexible tube through said first electrode wire guiding hole and extending outside said flexible tube between said first and second electrode wire guiding holes and then entering into said flexible tube through said second electrode wire guiding hole and then passing between the respective turns of said at least one pair of adjacent turns of said flexible coil which are located adjacent to said second electrode wire guiding hole, said intermediate portion of said electrode wire further extending through said flexible tube from said second electrode wire guiding hole to the proximal end of said flexible tube so that the second end of said electrode wire is at the proximal end of the flexible tube, and the second end of said electrode wire is adapted to be connected to a high frequency source.

2. An instrument according to claim 1, wherein said electrode wire extends out of said flexible tube from said one end of said flexible coil.

3. An instrument according to claim 2, wherein said flexible coil is integral with said electrode wire.

4. An instrument according to claim 2, wherein said one end of said flexible coil is fixed to said first end of said electrode wire.

5. An instrument according to claim 2, wherein said one end of said flexible coil is located closer to said distal end of said tube than said first electrode wire guiding hole and having at least another pair of turns located adjacent to said first electrode wire guiding hole, and said electrode wire extends in said flexible tube from the vicinity of said one end of said flexible coil and comes out of said flexible tube between said another pair of turns and through said first electrode wire guiding hole.

6. An instrument according to claim 5, wherein said flexible coil is integral with said electrode wire.

7. An instrument according to claim 5, wherein said one end of said flexible coil is fixed to said first end of said electrode wire.

8. An instrument according to claim 5, which further comprises a ring member fixed within said distal end portion of said flexible tube, and said first end of said electrode wire is fixed to said ring member.

9. An instrument according to any one of claims 1 to 8, wherein said flexible coil is a coil made of a resilient wire.

10. An instrument according to claim 9, wherein said flexible coil has gaps between respective adjacent turns thereof, the gap between any two adjacent turns of said flexible coil being substantially twice the diameter of said resilient wire.

11. An instrument according to claim 9, wherein said at least one pair of turns of said flexible coil which are located adjacent to said second electrode wire guiding hole are sparsely wound, whereas other turns of said flexible coil are densely wound.

12. An instrument according to claim 11, wherein said sparsely wound pair of turns have a gap between the turns thereof which is substantially twice the diameter of said resilient wire.

13. An instrument according to claim 11, wherein only said pair of turns of said flexible coil which are located adjacent to said second electrode wire guiding hole are separated from each other.

14. An instrument according to any of claims 5 to 8, wherein said at least another pair of turns of said flexible coil which are located adjacent said first electrode wire guiding hole and said at least one pair of turns of said flexible coil which are located adjacent said second electrode wire guiding hole are sparsely wound, whereas other turns of said flexible coil are densely wound.

15. An instrument according to claim 14, wherein each pair of the sparsely wound turns have respective gaps between the respective turns thereof which are substantially twice the diameter of said flexible wire.

16. An instrument according to claim 14, wherein only said pair of turns of said flexible coil which are located adjacent said first electrode wire guiding hole and said pair of turns located adjacent said second electrode wire guiding hole are sparsely wound.

17. An instrument according to claim 8, wherein said first end of said electrode wire is clamped between said ring member and the inner distal end portion of said flexible tube within which said ring member is fixed.

* * * * *